US012390360B2

(12) United States Patent
Bae et al.

(10) Patent No.: US 12,390,360 B2
(45) Date of Patent: *Aug. 19, 2025

(54) MALE CONDOM AND RING KIT

(71) Applicant: Edward Bae, Cerritos, CA (US)

(72) Inventors: Edward Bae, Rancho Palos Verdes, CA (US); Suk Wha Park, Rancho Palos Verdes, CA (US)

(73) Assignee: Edward Bae, Cerritos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/775,340

(22) Filed: Jul. 17, 2024

(65) Prior Publication Data

US 2024/0366419 A1    Nov. 7, 2024

Related U.S. Application Data

(63) Continuation of application No. 18/464,146, filed on Sep. 8, 2023, now Pat. No. 12,121,472.

(60) Provisional application No. 63/408,390, filed on Sep. 20, 2022, provisional application No. 63/509,347, filed on Jun. 21, 2023.

(51) Int. Cl.
*A61F 6/04* (2006.01)
*A61F 5/41* (2006.01)

(52) U.S. Cl.
CPC ............ *A61F 6/04* (2013.01); *A61F 5/41* (2013.01); *A61F 2005/414* (2013.01)

(58) Field of Classification Search
CPC ...... A61F 6/04; A61F 6/02; A61F 6/12; A61F 6/14; A61F 5/453; A61F 2006/047; A61F 5/41; A61F 2005/414; A61F 6/005; A61F 6/146; A61F 6/065; Y10S 128/918
See application file for complete search history.

(56) References Cited

U.S. PATENT DOCUMENTS

| 5,370,130 | A | | 12/1994 | Hess |
| 5,370,131 | A | * | 12/1994 | Hess ........................ A61F 6/04 |
| | | | | 128/842 |
| 5,715,839 | A | | 2/1998 | Strauss et al. |
| 2002/0121279 | A1 | | 9/2002 | Sanchez |
| 2005/0081863 | A1 | | 4/2005 | Lin |
| 2006/0124135 | A1 | | 6/2006 | Mayfield |

(Continued)

FOREIGN PATENT DOCUMENTS

| CN | 2636856 | 9/2004 |
| CN | 211633832 | 10/2020 |

(Continued)

OTHER PUBLICATIONS

Written Opinion and International Search Report for PCT/US2023/073798 Dated Nov. 16, 2023.

*Primary Examiner* — Ophelia A Hawthorne
(74) *Attorney, Agent, or Firm* — Concourse Law Group; Katherine B. Sales, Esq.

(57) ABSTRACT

A kit comprising at least one male condom having a condom base, a tubular sheath, and a reservoir tip, at least two wearable, silicone rings, each ring having an internal diameter that is different than the internal diameter of the other ring, and a single package comprising a first internal compartment and a second internal compartment, wherein the at least one male condom is contained in the first compartment, and the at least two wearable rings are contained in the second compartment.

28 Claims, 5 Drawing Sheets

(56) References Cited

U.S. PATENT DOCUMENTS

| | | | |
|---|---|---|---|
| 2007/0051373 A1 | 3/2007 | Lin | |
| 2013/0062226 A1* | 3/2013 | Lee | A61F 6/005 206/820 |
| 2014/0076329 A1* | 3/2014 | Rhodes | A61F 6/04 128/844 |

FOREIGN PATENT DOCUMENTS

| | | | | |
|---|---|---|---|---|
| DE | 4409721 A1 * | 9/1995 | | A61F 5/41 |
| DE | 29620141 | 5/1997 | | |
| DE | 102009031448 | 1/2011 | | |
| FR | 2743493 A1 * | 7/1997 | | A61F 6/04 |
| KR | 20160032683 | 3/2016 | | |
| WO | 2012003928 | 1/2012 | | |

* cited by examiner

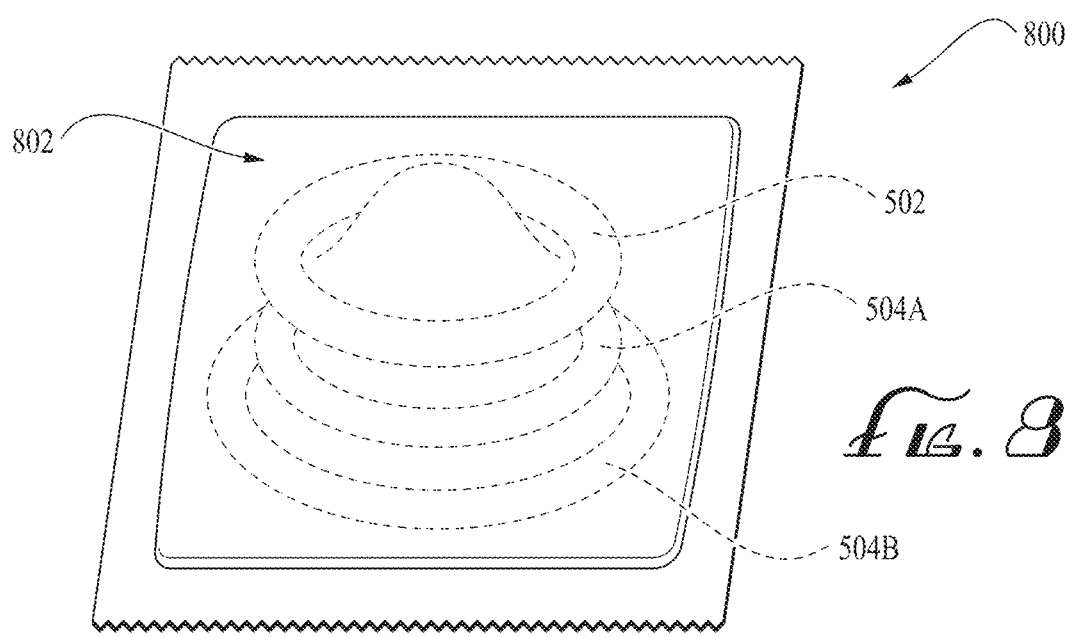
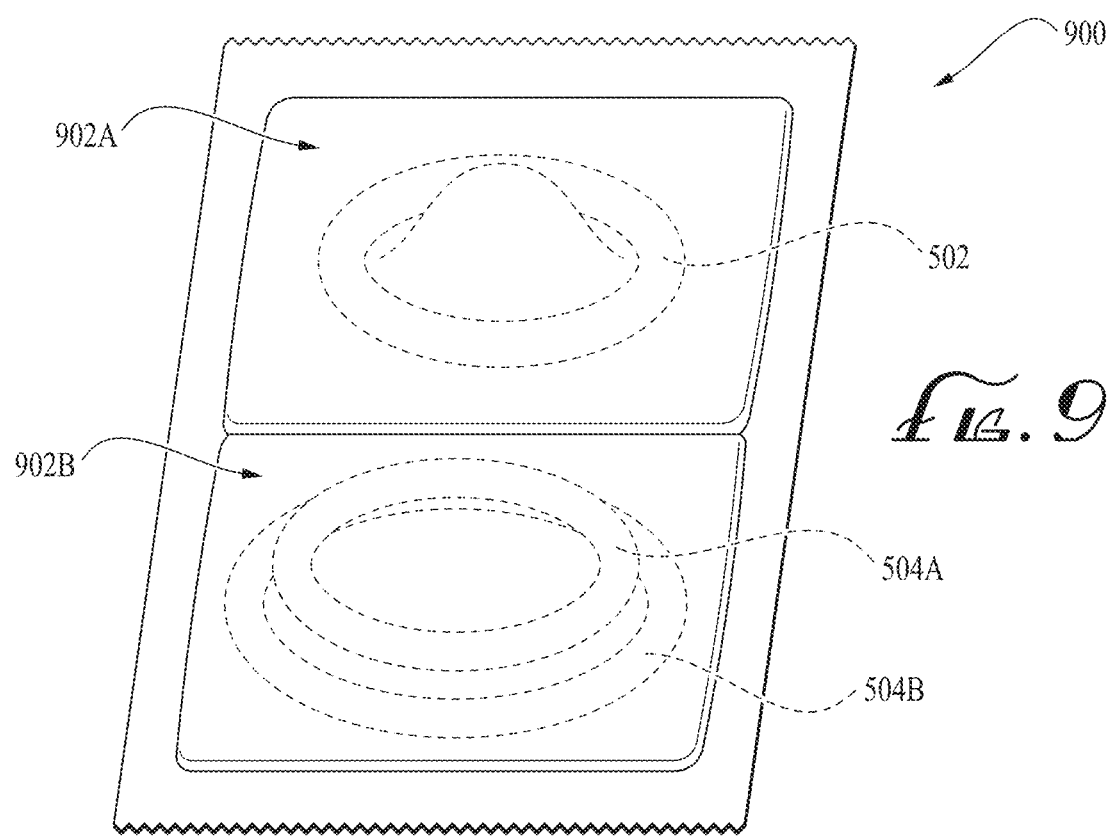

MALE CONDOM AND RING KIT

CROSS-REFERENCE TO RELATED APPLICATIONS

This application is a continuation of U.S. Non-Provisional patent application Ser. No. 18/464,146, titled "Male Condom and Ring Kit," filed Sep. 8, 2023, which claims priority to U.S. Provisional Patent Application No. 63/509,347, titled "Male Condom and Ring Combination," filed Jun. 21, 2023, and U.S. Provisional Patent Application No. 63/408,390, titled "Male Condom and Ring Combination," filed Sep. 20, 2022, the contents of which are incorporated by reference herein in their entirety.

BACKGROUND OF THE INVENTION

Male condoms are used to prevent transmission of disease and/or pregnancy when two individuals engage in sexual intercourse.

Additionally, there is a significant portion of the male population that suffers with some degree of erectile dysfunction (ED). A common solution to ED is the use of a ring placed around the shaft of the penis that applies pressure and ensures blood remains in the penis, helping to maintain an erection. It has also been found to be pleasurable to have the ring placed around both the testicles and the penis shaft as well. However, these two items (the condom and the ring) are always sold separately.

Accordingly, there is a need for a male condom and ring combination and/or kit.

SUMMARY

The present invention meets this need. In a first embodiment, the present invention is directed to a kit comprising at least one male condom, at least one wearable ring, and a single package. The male condom comprises a condom base, a tubular sheath, and an optional reservoir tip. The single package comprises at least one internal compartment, wherein the at least one condom and the at least one wearable ring are contained in the at least one internal compartment.

Optionally, the kit comprises at least two wearable rings.

Optionally, each ring has an internal diameter that is different than the internal diameter of the other ring.

Optionally, the package comprises a first internal compartment and a second internal compartment, and the at least one male condom is contained in the first compartment, and the at least two wearable rings are contained in the second compartment.

Optionally, the at least one ring is removably coupled to the condom base by at least one extension.

Optionally, the at least two wearable rings are removably coupled to each other by at least one extension, or optionally, at least two extensions.

Optionally, the wearable rings are made from silicone.

BRIEF DESCRIPTION OF THE DRAWINGS

These and other features, aspects, and advantages of the present invention will become better understood with regard to the following description, appended claims, and accompanying drawings.

FIG. 8 is a perspective view of a first alternative embodiment of the rings of the kit of FIG. 5; and FIG. 9 is a perspective view of a second alternative embodiment of the rings of the kit of FIG. 5.

DETAILED DESCRIPTION

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers ingredients or steps.

All dimensions specified in this disclosure are by way of example only and are not intended to be limiting. Further, the proportions shown in these Figures are not necessarily to scale. As will be understood by those with skill in the art with reference to this disclosure, the actual dimensions and proportions of any system, any device or part of a device disclosed in this disclosure will be determined by its intended use.

Figure 1:
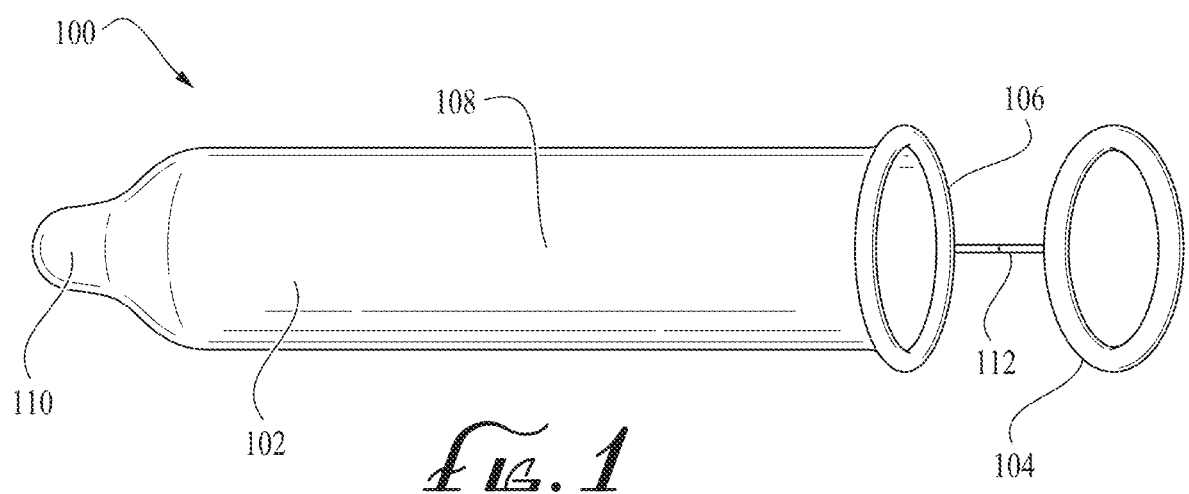
FIG. 1 is a side perspective view of a first embodiment of a male condom and ring kit having features of the present invention, wherein the ring is removably coupled to the condom.
Figure 2:
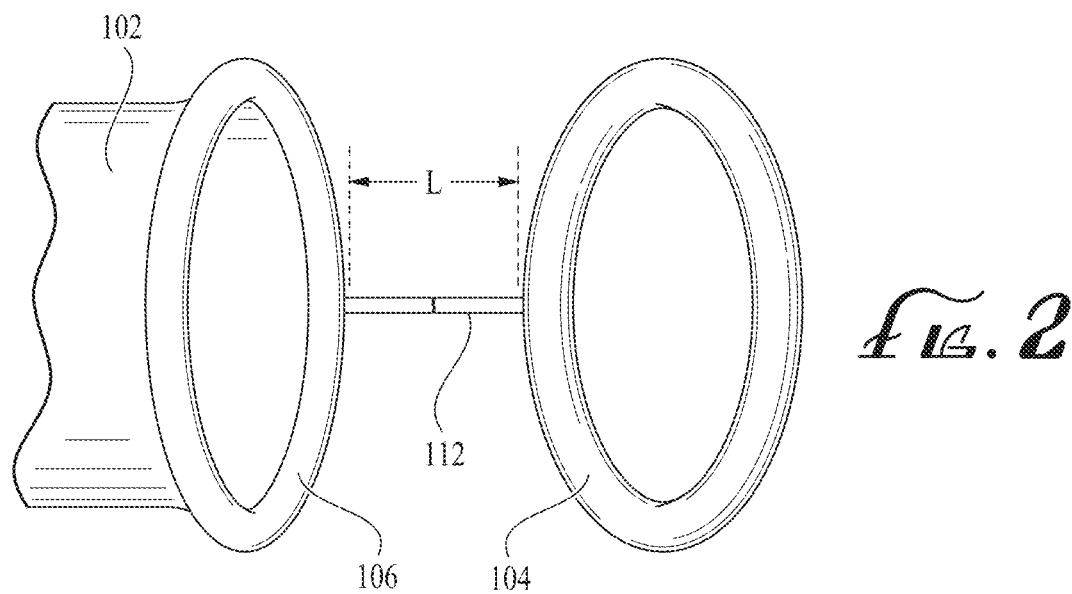
FIG. 2 is an enlarged view of a portion of the kit of FIG. 1.
Figure 3:
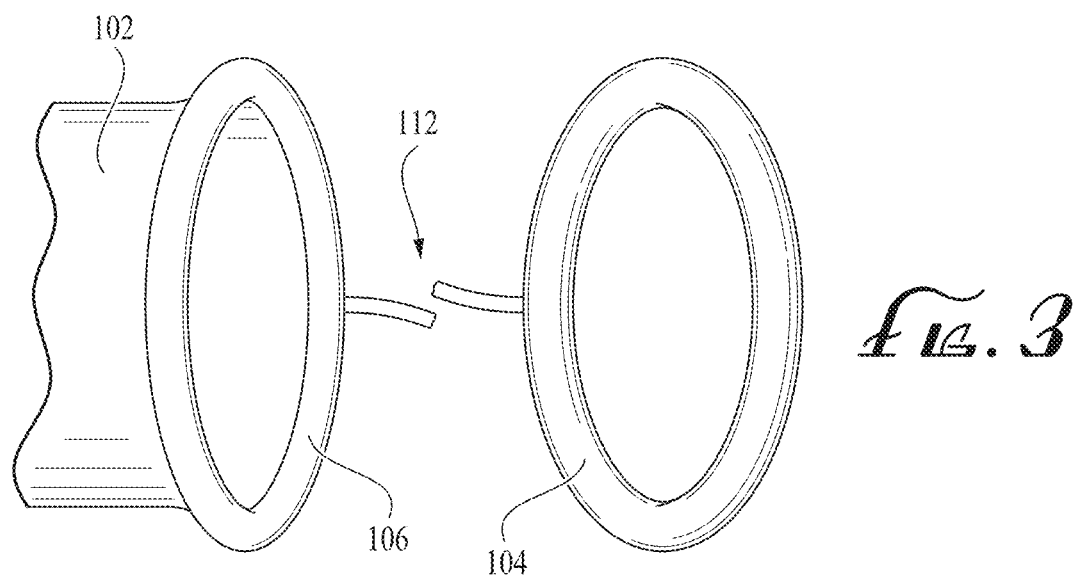
FIG. 3 is an additional enlarged view of a portion of the kit of FIG. 1.

Referring now to FIGS. 1-3, there is shown a first embodiment of a male condom and ring combination or kit 100 having features of the present invention. Specifically, the kit 100 comprises at least one male condom 102 having at least one wearable ring 104 coupled thereto. The male condom 102 has a condom base 106, a tubular sheath 108 and a reservoir tip 110 for receiving and collecting ejaculate. The condom 102 and the ring 104 can be made from a soft, comfortable and durable material such as polyurethane, thermoplastic elastomer (TPE), natural rubber latex, silicone, other suitable natural or synthetic materials, or any combination thereof.

Coupled to the condom base 106 is the at least one wearable ring 104. The ring 104 can in the shape of a smooth, symmetrical ring, having a smooth outer surface and a smooth inner surface, as shown in the drawings.

Optionally, the ring 104 can have one or more enlarged portions or nodes spaced around the ring 104 to apply additional pressure at one or more points around the penis and/or testicles. In this form, the ring 104 can have an undulating appearance/cross-section.

The ring 104 can be either permanently or removably coupled to the condom base 106 by one or more flexible extensions 112. Optionally, the extension 112 has elastic qualities, or made from an elastic material, that allows it to extend and retract if pulled upon. If removably coupled, the extension 112 can be breakable, such that the extension 112 can be broken, and the ring 104 can be physically separated from the condom 102 if the user should so choose. The extension 112 can be any length, but preferably the extension 112 can be about 1 to 3 inches in length, more preferably, about 1 to 1.5 inches in length.

A method of using the first embodiment 100 comprises the following steps: a) after an erection has been achieved, the user places the wearable ring 104 around the shaft of the penis, thereby reducing venous drainage from the penis. Optionally, the ring 104 is placed around both the shaft of the penis and the testicles, if so desired. Once the ring 104 is in place, the user then unrolls and applies the condom 102 in a known fashion to the penis.

Optionally, the user can first break the extension 112, then apply the ring 104, then apply the condom 102.

Figure 4:
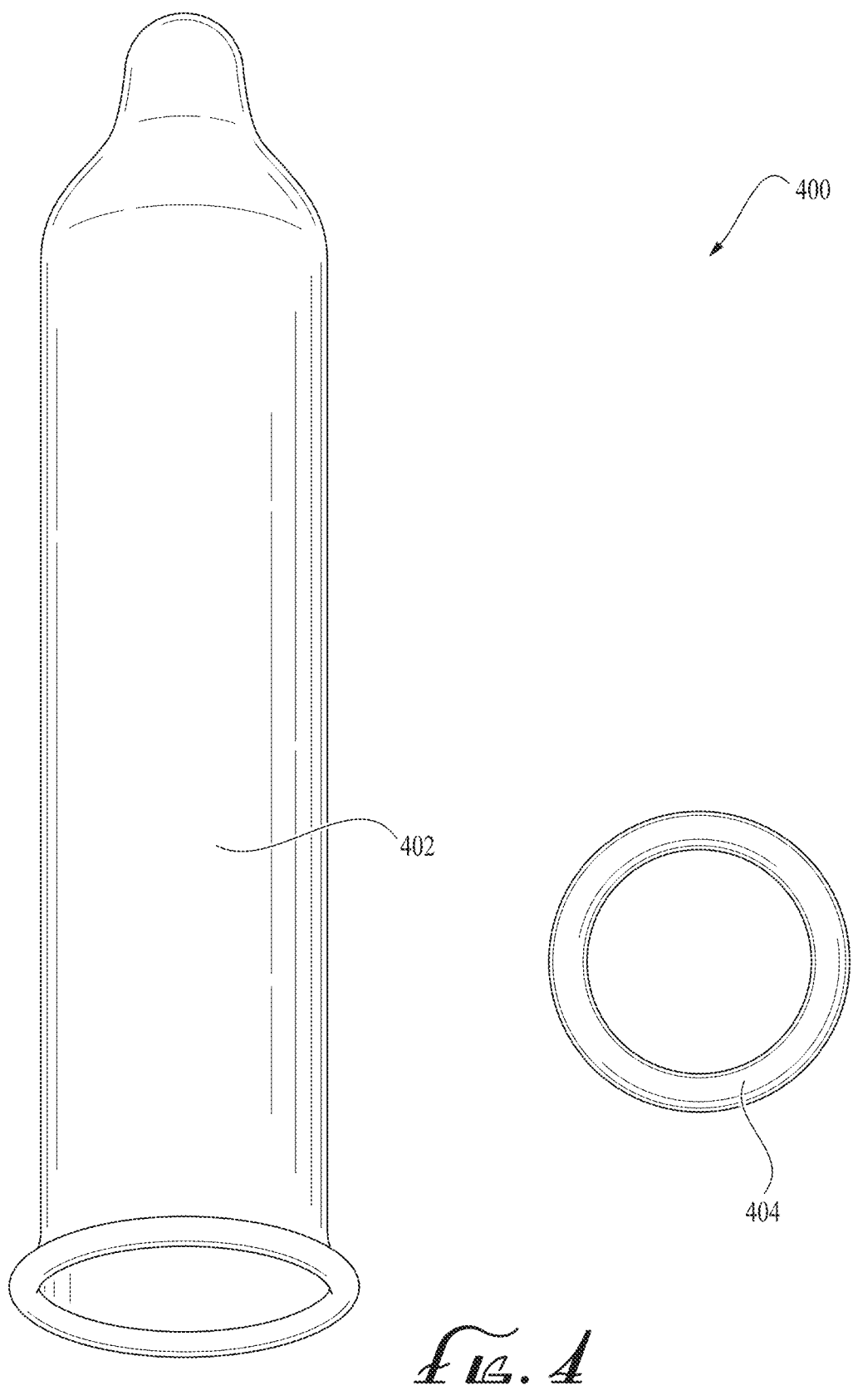
FIG. 4 is a front perspective view of a second embodiment of a male condom and ring kit having features of the present invention, wherein the ring is not coupled to the condom.

Referring now to FIG. 4, there is shown a second embodiment of the male condom and ring kit 400. In this embodiment, the condom 402 and the ring 404 are not connected to each other by an extension and are instead packaged and sold as a combination. The condom 402 and ring 404 can be packaged individually and sold together, or packaged in the same container/pouch.

Figure 5:
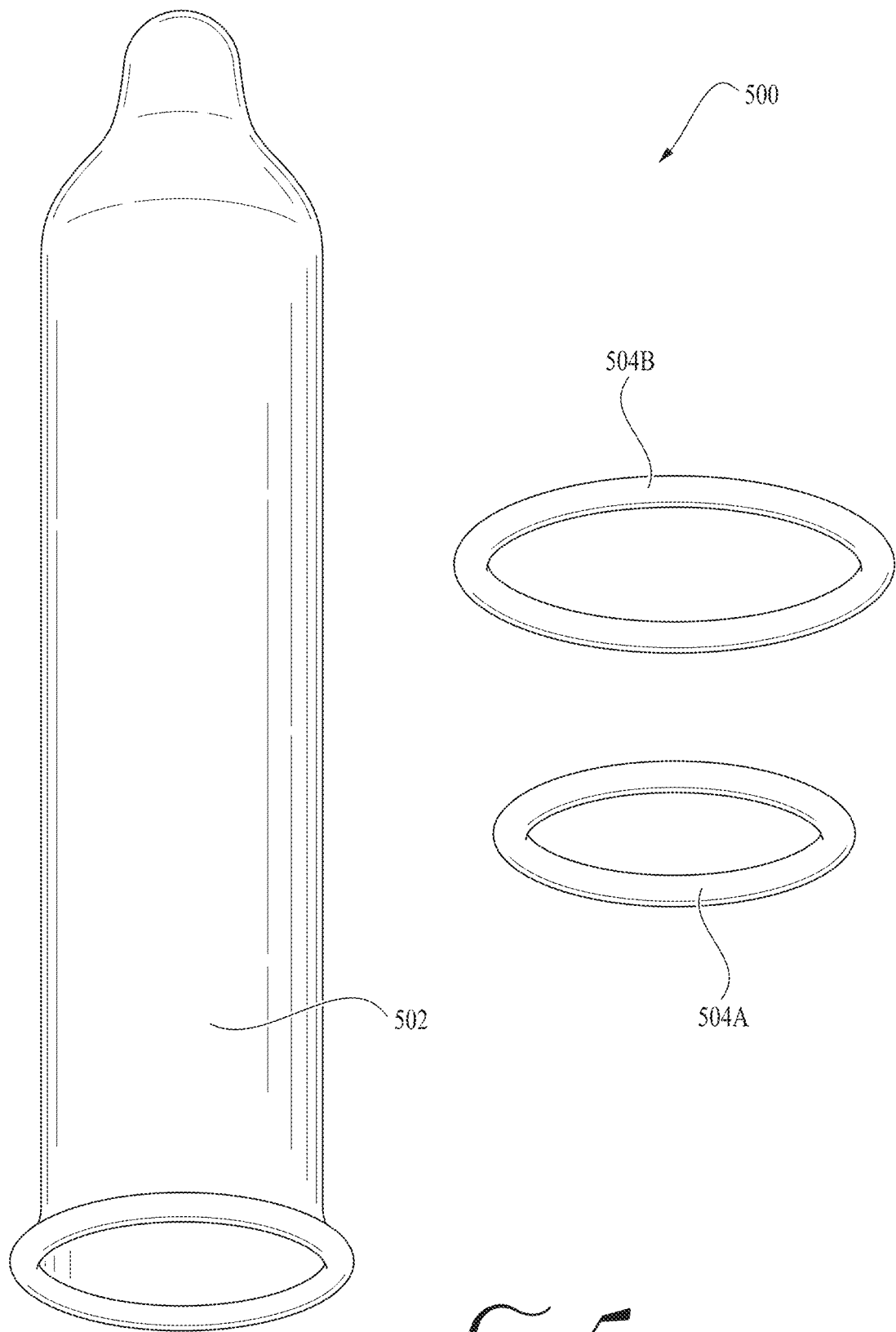
FIG. 5 is a front perspective view of a third embodiment of a male condom and ring kit having features of the present invention, wherein the kit comprises two rings.

Referring now to FIG. 5, there is shown a third embodiment of the male condom and ring kit 500. In this embodiment, the kit 500 comprises at least one condom 502 and at least one ring 504, but preferably two or more rings 504A, 504B. While the two or more rings 504A, 504B can have the same diameter, preferably, the two rings 504A, 504B have two different diameters such that they are two different "sizes" and this allows the user to choose the ring 504 that is best suited to meet their desires.

Figure 6:
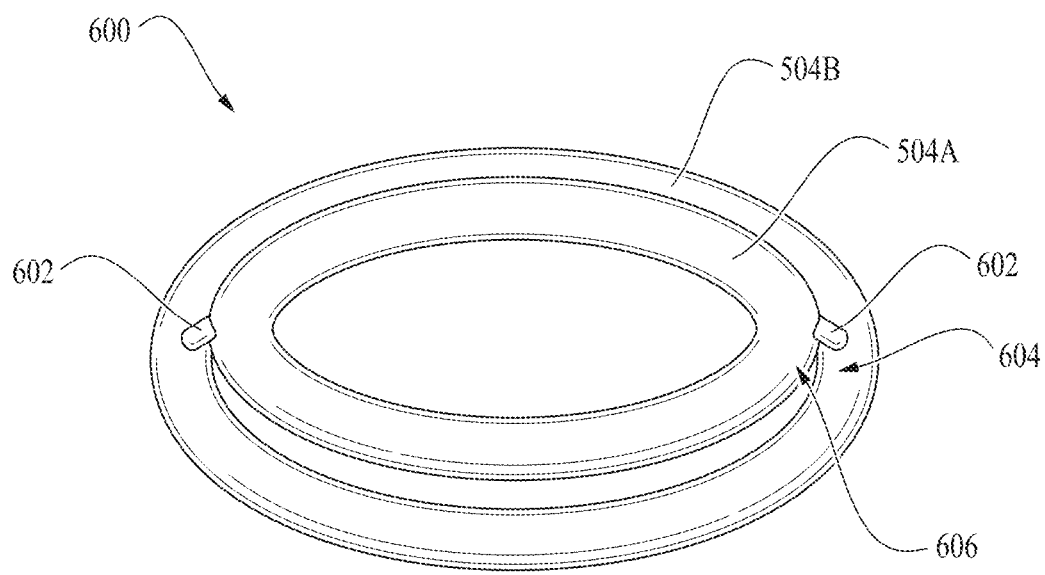
FIG. 6 is a perspective view of a first form of packaging the kit of FIG. 5.
Figure 7:
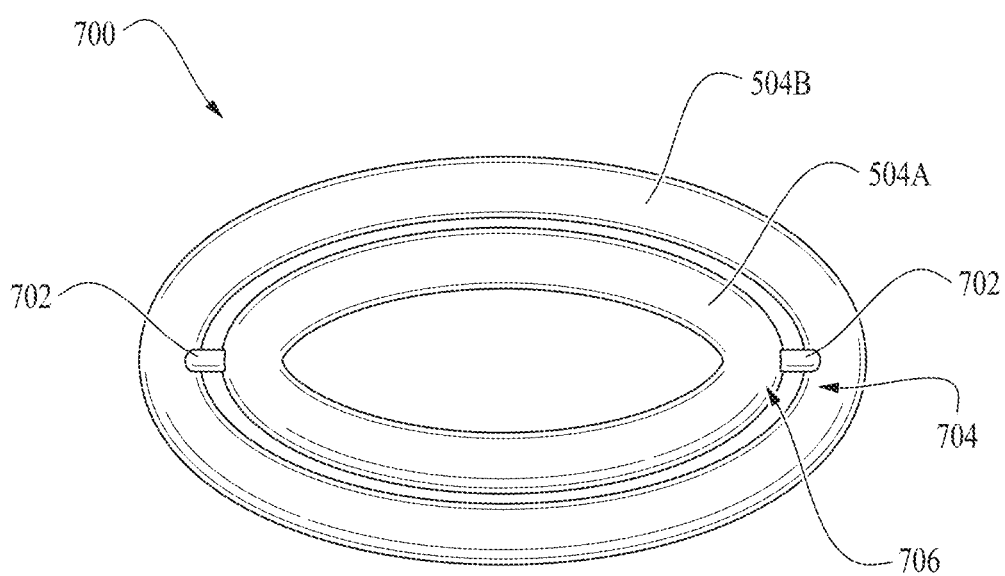
FIG. 7 is a perspective view of a second form of packaging the kit of FIG. 5.

Referring now to FIGS. 6 and 7, there is shown two different configurations of the two or more rings 504A, 504B of the kit 500 of FIG. 5. The two or more rings 504A, 504B can either be physically separate from each other, as shown in FIG. 5, or the rings 504 can be physically coupled to each other, as shown in FIGS. 6 and 7, via one or more extensions 602, 702. The extensions 602, 702 are configured to break when a user attempts to separate the rings 504A, 504B from each other.

In FIG. 6, the rings 504A, 504B are stacked on top of each other, such that the smaller diameter ring 504A is positioned slightly above the larger diameter ring 504B. In this configuration, the extensions 602 are positioned to angle slightly upward from an upper surface 604 of ring 504B and couple to ring 504A along a lower side surface 606. This slight angle of the extension 602 relative to the rings 504A, 504B can be seen in FIG. 6.

In FIG. 7, ring 504A with the smaller diameter is nested within ring 504B with the larger diameter, such that their top surfaces are relatively flush with another and the nested pair of rings 504A, 504B lay relatively flat. In this configuration, the extensions 702 extend substantially horizontally from an inside surface 704 of ring 504B to an outside surface 706 of ring 504A. This horizontal orientation of the extensions 702 relative to the rings 504A, 504B can be seen in FIG. 7.

Referring now to FIGS. 8 and 9, there is shown two different forms of packaging the embodiments shown in FIGS. 1 through 7.

In FIG. 8, there is shown a single package 800 with a single internal compartment 802. Within that single compartment 802, there is the one or more, preferably two or more, rings 504A, 504B stacked on top of at least one rolled male condom 502. Due to the differences in diameter, ideally the condom 502 is on the bottom of the stack, ring 504B with the larger diameter is then placed on top of the condom 502, and ring 504A with the smaller diameter (relative to ring 504B) is placed on top of ring 504B. It should be noted that any of the aforementioned ring and condom combinations 100, 400, 500, 600, 700 can be packaged in the manner shown in FIG. 8.

In FIG. 9, there is shown a single package 900 having at least two internal compartments 902A, 902B that are physically separated from each other, but are part of the same overall package 900. In this configuration, the at least one rolled condom 502 is in the first compartment 902A, and the one or more, preferably two or more rings 504A, 504B are in the second compartment 902B. The two or more compartments 902A, 902B are not limited to the side-by-side configuration shown in FIG. 9, and it should be noted that the compartments 902A, 902B can be orientated in any manner that a person of ordinary skill in the art would appreciate.

Both packaging embodiments 800, 900 can be in the form of known male condom packaging that is made from a plastic or metal foil material that can be easily to torn to access its contents. Optionally, one more sides of the packaging 800, 900 can be clear or opaque so that the contents of the packaging 800, 900 can be viewed by the user prior to opening the packaging 800, 900.

The present invention has the following advantages:

Because the ring or rings 504 come packaged with the condom 502 already, the user only has to make one purchase. Moreover, while condoms 502 are typically sold at many different establishments, such as gas stations, grocery stores, and drug stores, it can be harder to find a retailer selling wearable rings 504. Accordingly, the present invention meets this need by providing both items in the same package 800, 900.

Additionally, while many users desire to utilize wearable rings 504, different users have different size requirements. The kit 500 of the present invention provides the option of having two different sized rings come with the condom. The user can then select the ring that is best suited to their needs, without having to separately purchase a ring, or rings, and guess which size is best.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference.

What is claimed is:

1. A kit comprising:
   a) at least one male condom;
   b) at least one wearable constriction device that is physically separate from the condom, wherein the at least one wearable constriction device forms a single opening; and c) a single package comprising a first internal compartment and a second internal compartment, wherein the at least one male condom is contained in the first compartment, and the at least one constriction device is contained in the second compartment.

2. The kit of claim 1, wherein the kit comprises at least two constriction devices.

3. The kit of claim 2, wherein the at least two constriction devices comprise at least two rings.

4. The kit of claim 3, wherein each ring has an internal diameter that is different than the internal diameter of the other ring.

5. The kit of claim 3, wherein the at least two wearable rings are detachably coupled to each other by at least one extension.

6. The kit of claim 3, wherein the at least two wearable rings are detachably coupled to each other by at least two extensions.

7. The kit of claim 1, wherein the at least one constriction device comprises a ring.

8. The kit of claim 1, wherein the at least one wearable constriction device is made from silicone.

9. The kit of claim 1, wherein the at least one wearable constriction device is made from silicone.

10. A kit comprising:
    a) at least one male condom;
    b) at least one wearable constriction device that is physically separate from the condom, wherein the at least one wearable constriction device forms a single opening; and
    c) a single package comprising at least one internal compartment, wherein the at least one condom and the at least one wearable constriction device are contained in the at least one internal compartment.

11. The kit of claim 10, wherein the kit comprises at least two constriction devices.

12. The kit of claim 11, wherein the at least two constriction devices comprise at least two rings.

13. The kit of claim 12, wherein each ring has an internal diameter that is different than the internal diameter of the other ring.

14. The kit of claim 12, wherein the at least two wearable rings are detachably coupled to each other by at least one extension.

15. The kit of claim 12, wherein the at least two wearable rings are detachably coupled to each other by at least two extensions.

16. The kit of claim 10, wherein the at least one constriction device comprises a ring.

17. The kit of claim 10, wherein the at least one constriction device is made from silicone.

18. A kit comprising:
    a) at least one male condom, the at least one male condom having:
       i) a condom base; and
       ii) at least one tubular sheath;
    b) at least one wearable constriction device that is physically separate from the condom, wherein the at least one wearable constriction device are physically separate from each other; and
    c) a single package comprising at least one internal compartment, wherein the at least one condom and the at least one wearable constriction device are contained in the at least one internal compartment.

19. The kit of claim 18, wherein the kit comprises at least two constriction devices.

20. The kit of claim 19, wherein the at least two constriction devices comprise at least two rings.

21. The kit of claim 20, wherein each ring has an internal diameter that is different than the internal diameter of the other ring.

22. The kit of claim 18, wherein the at least one constriction device comprises a ring.

23. The kit of claim 18, wherein the at least one constriction device is made from silicone.

24. A kit comprising:
    a) at least one male condom, the at least one male condom having:
       i) a condom base; and
       ii) a tubular sheath;
    b) at least one wearable constriction device that is physically separate from the condom, wherein the at least one wearable constriction device are physically separate from each other; and
    c) a single package comprising a first internal compartment and a second internal compartment, wherein the at least one male condom is contained in the first compartment, and the at least one constriction device is contained in the second compartment.

25. The kit of claim 24, wherein the kit comprises at least two constriction devices.

26. The kit of claim 25, wherein the at least two constriction devices comprise at least two rings.

27. The kit of claim 26, wherein each ring has an internal diameter that is different than the internal diameter of the other ring.

28. The kit of claim 24, wherein the at least one constriction device comprises a ring.

* * * * *